United States Patent [19]

Lipton et al.

[11] Patent Number: 5,282,791
[45] Date of Patent: Feb. 1, 1994

[54] DEVICE TO SECURE A SURGICAL INSTRUMENT AND METHOD

[75] Inventors: J. M. Lipton, Dallas; J. D. Inman; C. E. Ward, Jr., both of Ft. Worth, all of Tex.

[73] Assignee: Board of Regents, The University of Texas System, Austin, Tex.

[21] Appl. No.: 864,660

[22] Filed: Apr. 7, 1992

[51] Int. Cl.$^5$ .............................................. A61M 25/02
[52] U.S. Cl. ........................... 604/180; 128/DIG. 26
[58] Field of Search .................. 604/174, 179, 180; 128/DIG. 6, DIG. 26

[56] References Cited

U.S. PATENT DOCUMENTS

| | | | |
|---|---|---|---|
| 3,645,835 | 2/1972 | Hodgson | 161/146 |
| 3,918,446 | 11/1975 | Buttaravoli | 604/180 |
| 4,096,863 | 6/1978 | Kaplan et al. | 128/349 R |
| 4,165,748 | 8/1997 | Johnson | 128/348 |
| 4,275,721 | 6/1981 | Olson | 604/180 |
| 4,583,976 | 4/1986 | Ferguson | 604/174 |
| 4,614,183 | 9/1986 | McCracken et al. | 128/132 R |
| 4,669,458 | 6/1987 | Abraham et al. | 604/180 |
| 4,678,462 | 7/1987 | Vaillancourt | 604/180 |
| 4,704,177 | 11/1987 | Vaillancourt | 604/180 |
| 4,838,868 | 6/1989 | Forgar et al. | 604/180 |
| 4,875,896 | 10/1989 | Kurtz | 128/DIG. 26 |
| 4,898,587 | 2/1990 | Mera | 604/180 |
| 5,116,324 | 5/1992 | Brierley et al. | 604/180 |

*Primary Examiner*—Paul J. Hirsch
*Attorney, Agent, or Firm*—Harry C. Post, III

[57] ABSTRACT

A device to secure a surgical instrument to a patient that comprises an elongated flexible body. A first quantity of adhesive substance is disposed on the body to adhere a portion of the body to the patient. A second quantity of adhesive substance is disposed on the body to adhere a portion of the surgical instrument to the body. A method of securing a surgical instrument to a patient, comprising the steps of inserting a first portion of the surgical instrument into the patient. A first portion of an elongated flexible material is then secured to a patient. A second portion of the elongated flexible material is folded over a second portion of the surgical instrument. The second portion of the elongated flexible material is secured to the first portion of the elongated flexible material.

1 Claim, 2 Drawing Sheets

5,282,791

DEVICE TO SECURE A SURGICAL INSTRUMENT AND METHOD

TECHNICAL FIELD

This invention relates to a device to secure a surgical instrument to a patient and a method of securing a surgical instrument to a patient and; more particularly, to a pressure sensitive adhesive device for securing a surgical instrument to a patient and a method using a pressure sensitive adhesive device in securing a surgical instrument to a patient.

BACKGROUND ART

It has been common practice to attach a surgical instrument, such as a needle or a catheter, to a patient by taping the instrument to the patient after the needle or tubular portion has been inserted into the patient. Although this procedure secures the instrument to the patient, it does not correctly orient the tube and an excess of adhesive bandage may be utilized. Further, this procedure fails to prevent the hub portion of the surgical instrument from contacting with and possibly injuring the patient. This procedure also endangers the health care provider by subjecting him or her into contact with the blood of the patient because the rubber gloves worn by the health care provider must be removed to attach the adhesive tape. The adhesive tape sticks to latex gloves causing a need for the removal of the gloves, which endangers the health care provider. Utilization of adhesive tape also causes tears in the gloves.

A recent development in this area is a band for anchoring a catheter or any other tubular device to the body described in U.S. Pat. No. 4,096,863 issued to David Kaplan, et al. This band only applies to a limb and incorporates a strap to secure the strap to a limb and a secondary strap to form a closed loop to encircle the catheter or similar device and hold it securely in place on the limb. Since this band only operates on a limb, it is not as useful as desirable. Further, since the band is narrow, this catheter holder fails to prevent the hub of the catheter from engaging the patient. Further, it uses a fastener, which makes it difficult to manufacture and expensive. Further, since it requires two bands to be operable, when one of the bands is lost, which may occur in emergency situations, such device becomes inoperable. Further, it is difficult to use without removing one's rubber gloves, which makes the health care provider susceptible to contact with the blood of the patient.

Another development in this area is a catheter tube holder described in U.S. Pat. No. 4,165,748, issued in the name of Melissa C. Johnson. The holder uses a pair of main members connected by a narrow bridge with complementary fasteners on the nonadhesive side of the bridge to hold the bridge in a chosen position. Because the bridge is narrow, which makes this tube holder fail to prevent the hub of the catheter from engaging the patient. Further, it uses a fastener, which may become inoperable in emergency situations and makes is difficult to manufacture and expensive. Further, the holder is difficult to use without removing one's rubber gloves, which makes the health care provider susceptible to contact with the blood of the patient.

A development in the area of adhesive film dressings is described in U.S. Pat. No. 4,614,183 issued to Robert W. McCracken, et al. In this patent, an adhesive film dressing is described in which a film has one side coated with an adhesive and three release papers covering the adhesive. An edge flap is provided on each of the release papers so that each paper may be individually grasped and removed. This patent does not describe a catheter securing device, does not describe a device that inhibits the injury to a patient by preventing a catheter hub from contacting the patient, and does not describe a device that allows a health care provider to secure a surgical device to a patient without removing one's rubber gloves.

Accordingly, it is an object of the present invention to provide a device to secure a surgical instrument to a patient that prevents undesirable contact between parts of the surgical instrument and the patient.

Further, it is an object of the present invention to provide a device that enables the health care provider to not remove their rubber gloves when securing a surgical instrument to a patient.

Further, it is an object of the present invention to provide a device to secure a surgical instrument to a patient with a passageway to inhibit damage to the patient.

Further, it is an object of the present invention to provide a device to secure a surgical instrument to a patient allowing the surgical instrument to be viewed after being secured to the patient.

Further, it is an object of the present invention to provide a method of securing a surgical instrument to a patient.

DISCLOSURE OF THE INVENTION

In accordance with the present invention, there is provided a device to secure a surgical instrument to a patient. The device comprises an elongated flexible body including first and second surfaces facing away from one another. Provided on the body is a protecting portion that has a length and width sufficient to prevent contact of a portion of the surgical instrument with the patient, a securing portion that has a length sufficient to extend across the portion of the surgical instrument and an intermediate portion extending between the protecting and securing portions. A first quantity of adhesive substance is disposed on the first surface of the body to adhere the protecting portion of the body to the patient. A second quantity of adhesive substance is disposed on the second surface of the body to adhere the portion of the surgical instrument between the protecting and securing portions of the body when the securing portion is folded over and onto the protecting portion.

Further, in accordance with the present invention there is provided a device to secure a surgical instrument to a patient. The device comprises an elongated flexible body including a protecting portion defining a passageway sufficient to receive a first portion of the surgical instrument, the protecting portion having a length and width sufficient to prevent contact of a second portion of the surgical instrument with the patient, a securing portion, and an intermediate portion. A first quantity of adhesive substance is disposed on the body to adhere the protecting portion of the body to the patient. A second quantity of adhesive substance is disposed on the body to adhere the second portion of the surgical instrument between the protecting and securing portions of the body.

Further, in accordance with the present invention there is provided a device to secure a surgical instrument to a patient. The device comprises an elongated body. A first quantity of adhesive substance is disposed on the body to adhere a portion of the body to the patient. A second quantity of adhesive substance is disposed on the body to adhere a portion of the surgical instrument to the body. A first sheet of protective material covers the first quantity of adhesive substance with the first sheet including a tab extending beyond the first quantity of adhesive substance by a distance sufficient to allow the tab to be gripped by a finger and thumb encased within a rubber glove. A second sheet of protective material covers the second quantity of adhesive substance with the second sheet including a tab extending beyond the second quantity of adhesive substance by a distance sufficient to allow the tab to be gripped by a finger and thumb encased within a rubber glove.

Further, in accordance with the present invention there is provided a method of securing a surgical instrument to a patient. The method comprises the steps of inserting a first portion of the surgical instrument into the patient. A first portion of an elongated flexible material is then secured to the patient beneath a second portion of the surgical instrument with the first portion of the surgical instrument extending through a passageway in the elongated flexible material. A second portion of the elongated flexible material is folded over a second portion of the surgical instrument. The second portion of the elongated flexible material is secured to the first portion of the elongated flexible material.

BRIEF DESCRIPTION OF THE DRAWINGS

Other objects and advantages of the invention will become apparent upon reading the following detailed description and upon reference to the drawings, wherein like reference characters are used throughout to designate like parts.

BEST MODE FOR CARRYING OUT THE INVENTION

Figure 1:
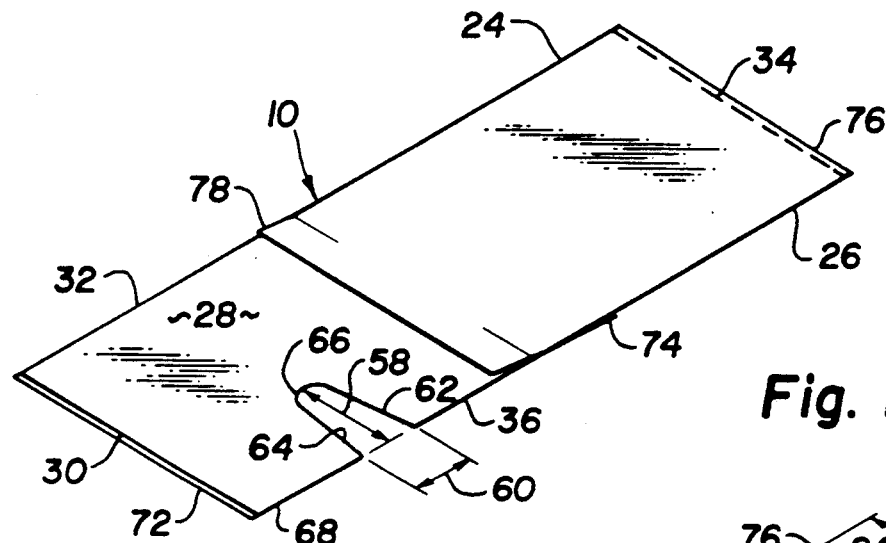
FIG. 1 is a perspective view of a device to secure a surgical instrument to a patient constructed according to the present invention.
Figure 2:
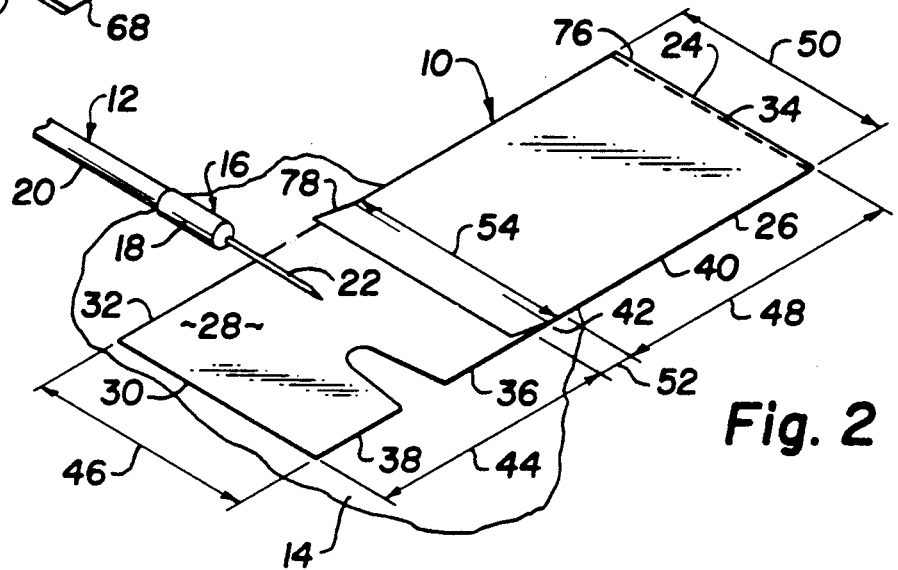
FIG. 2 is a perspective view of a first portion of the device shown in FIG. 1 secured to a patient and a surgical instrument positioned for inserting into the patient.
Figure 3:
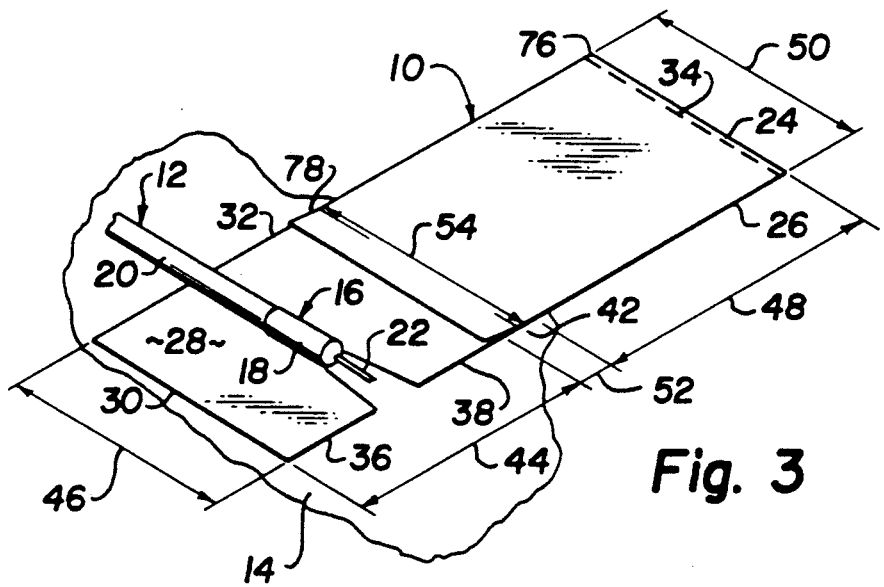
FIG. 3 is a perspective view of a first portion of the device shown in FIG. 1 secured to a patient and the surgical instrument inserted into the patient.
Figure 4:
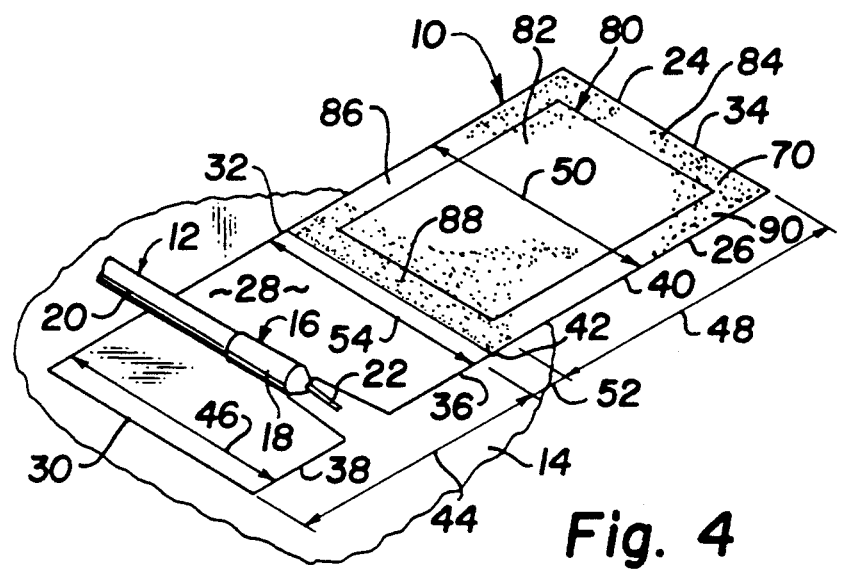
FIG. 4 is a perspective view of a first portion of the device shown in FIG. 1 secured to a patient, the surgical instrument inserted into the patient and a sheet of protective material removed from the device shown in FIG. 1.

Turning now to the drawing, there is shown a device 10 to secure a surgical instrument 12 to the skin of a patient 14.

Surgical instrument 12, such as a catheter, is of conventional design having a first portion 16 formed by a hub 18 that interconnects a body 20 of the catheter with a needle 22, which forms a second portion of the catheter. When a catheter is inserted into patient 14, the patient can be injured when hub 18 abrades the patient's skin as well as when needle 22 is inappropriately moved after being inserted into the patient.

Device 10 has an elongated, rectilinear and flexible body 24. Body 24 is defined by first and second surfaces 26 and 28, respectively, facing away from one another. Body 24 is further defined by first, second, third and fourth sides, 30, 32, 34 and 36, respectively. The four sides being connected to one another to form an angle of substantially 90°. Further, first side 30 and third side 34 extend substantially parallel to one another, and second side 32 and fourth side 36 extend substantially parallel to one another.

Also included in body 24 are a protecting portion 38, a securing portion 40, and an intermediate portion 42 extending from the second to the fourth sides between the protecting and securing portions.

Protecting portion 38 has a length 44 extending between first side 30 and intermediate portion 42, preferably length 44 is slightly less than ½ the distance from first side 30 to fourth side 34, and a width 46 extending between second side 32 and fourth side 36. Further, length 44 and width 46 are sufficient to prevent contact of first portion 16, including hub 18, of surgical instrument 12 with patient 14.

Securing portion 40 has a length 48 extending between intermediate portion 42 and third side 34, preferably length 48 is slightly less than ½ the distance from first side 30 to fourth side 34, and a width 50 extending between second side 32 and fourth side 36. It is preferred that length 48 is sufficient to extend across first portion 16 of surgical instrument 12 and width 50 is the same as width 46.

Intermediate portion 42 has a length 52 that is made up of the difference of the sum of lengths 44 and 48 from the distance between first side 30 and third side 34, which is preferably only sufficient to allow securing portion 40 to be easily folded onto protecting portion 38. Further, intermediate portion 42 has a width 54 extending between second side 32 and fourth side 36, which is preferably the same as widths 46 and 50.

Also, defined in body 24 is a passageway 56 extending from first surface 26 to second surface 28 in protecting portion 38. Passageway 56 includes a length 58 and width 60 sufficient to receive second portion 22 of surgical instrument 12. Passageway 56 is a generally V-shaped notch with the V-shape having first and second legs 62 and 64, respectively, extending from fourth side 36 of protecting portion 38 of body 24. An arcuate top 66 forms part of the V-shape and connects first and second legs 62 and 64, respectively, and length 58 extends into body 24 by a distance sufficient to dispose second portion 22 of surgical instrument 12 between fourth side 36 of body 24 and top 66 of the V-shaped notch.

A first quantity of pressure adhesive substance 68, preferably, a contact adhesive substance, is disposed on first surface 26 of body 24 and over the area defined by protecting portion 38 to adhere protecting portion 38 of body 24 to the skin of patient 14.

A second quantity of pressure adhesive substance 70, preferably a contact adhesive substance, is disposed on second surface 28 of body 24 and over the area defined by securing portion 40 to adhere first portion 16 of surgical instrument 12 between protecting portion 38 and securing portion 40 of body 24 when securing portion 40 is folded over and onto protecting portion 38.

A first sheet of protective material 72 is used to prevent undesirable contact of adhesive substance 68 with objects such as gloves. First sheet 72 is disposed to face first surface 26 and has a size (length and width) at least sufficient to cover first quantity of adhesive substance 68. First sheet 72 may be constructed to have a size sufficient to allow the overlapping of sides 30, 32 and 36 of protection portion 38 of body 24. Even though sides 30, 32 and 36 are not overlapped, a lip 74 is provided on sheet 72 to extend beyond first quantity of adhesive substance 68 by a distance sufficient to allow the lip to be gripped by a finger and thumb encased within a rubber glove of a person applying device 10 to a patient 14. Preferably, lip 74 is disposed to extend over intermediate portion 42 of body 24.

A second sheet of protective material 76 is used to prevent undesirable contact of second quantity of adhesive substance 70 with objects, such as gloves. Second sheet 76 is disposed to face second surface 28 and has a size (length and width) at least sufficient to cover second quantity of adhesive substance 70. Second sheet 76 may be constructed to have a size sufficient to allow the overlapping of sides 32, 34 and 36 of protection portion 38. Even though no overlap of sides 32, 34 and 36 is provided, a lip 78 is provided on second sheet 76 to extend beyond second quantity of adhesive substance 70 by a distance sufficient to allow the lip to be gripped by a finger and thumb encased within a rubber glove of a person applying device 10 to patient 14. Preferably, lip 78 is disposed to extend over intermediate portion 42 of body 24.

When securing surgical instrument 12 to patient 14, first portion 38 of elongated flexible body 24 is secured to patient 14. A portion 22 of surgical instrument 12 is inserted through passageway 56 provided in first portion 38 of elongated flexible body 24. A second portion 40 of elongated flexible body 24 is folded over another portion 18 of surgical instrument 12. Second portion 40 of elongated flexible body 24 is secured to first portion 38 of elongated flexible body 24.

To remove first sheet of protective material 72 from first quantity of adhesive substance 68 prior to securing first portion 38 of elongated flexible body 24 to patient 14, a user wearing gloves grasps lip 74 on first sheet of protective material 72 to lift and remove first sheet 72 from device 10.

To remove second sheet of protective material 76 from second quantity of adhesive substance 70 prior to securing second portion 40 of elongated flexible body 24 to first portion 38, a user wearing gloves grasps lip 78 on second sheet of protective material 76 to lift and remove second sheet 76 from device 10.

Figure 5:
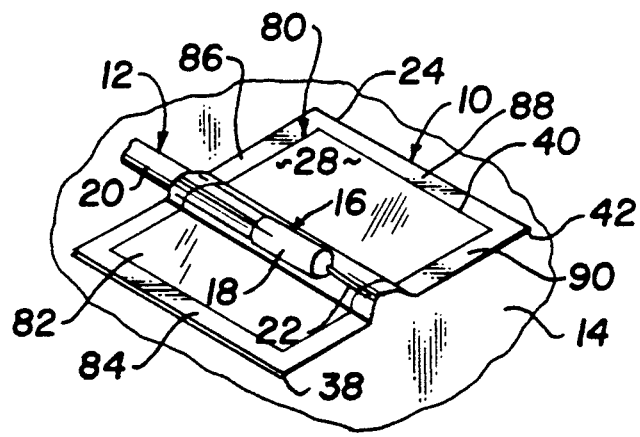
FIG. 5 is a perspective view of a first portion of the device shown in FIG. 1 secured to a patient, the surgical instrument inserted into the patient and a second portion of the device shown in FIG. 1 secured to the first portion.

As shown in FIG. 5, disposed within securing portion 40 is a viewing portion 80 to permit observation of hub 18, catheter 20 and needle 22 and that portion of patient 14 positioned beneath passageway 56. Viewing portion 80 defines a window 82 that is circumscribed by first edge 84, second edge 86, third edge 88 and fourth edge 90 of securing portion 40 of body 24. As shown, first edge 84 and third edge 88 extend in a parallel direction with one another and second edge 86 and fourth edge 90 extend in a parallel direction with one another to, thereby, form a rectilinear viewing area through securing portion 40 of body 24. In order for hub 18, catheter 20 and needle 22 and that portion of patient 14 positioned beneath passageway 56 to be viewed, second quantity of adhesive substance 70 is made from a transparent material.

The invention having been described, what is claimed is:

1. A device to secure a surgical instrument to a patient, comprising: an elongated, rectilinear and flexible body defined by first and second surfaces facing away from one another, first, second, third and fourth sides, the first and third sides extending substantially parallel to one another and the second and fourth sides extending substantially parallel to one another, said body including a protecting portion to prevent contact of a first portion of the surgical instrument with the patient, a securing portion, a viewing portion disposed in the securing portion for observing the first portion of the surgical instrument, the viewing means being made from a transparent material defining a window circumscribed by the securing portion, and an intermediate portion extending from the second to the fourth sides between the protecting and securing portions, the protecting portion having a length extending between the first side and intermediate portion and a width extending between the second and fourth sides, the length and width being sufficient to prevent contact of the first portion of the surgical instrument with the patient, the securing portion having a length extending between the intermediate portion and the third side and being sufficient to extend across the first portion of the surgical instrument, and said body defining a passageway through the protecting portion, the passageway including a length and width sufficient to receive a second portion of the surgical instrument, the passageway defined in said body being a generally V-shaped notch, the V-shaped notch having first and second legs extending from the fourth side of the protecting portion of said body, an arcuate top connecting the first and second legs and a length extending into said body by a distance sufficient to dispose the second portion of the surgical instrument between the fourth side of said body and the top of the notch; a first quantity of pressure adhesive substance disposed on the first surface of said body to adhere the protecting portion of said body to the patient; a second quantity of pressure adhesive substance disposed on the second surface of said body to adhere the portion of the surgical instrument between the protecting and securing portions of said body when the securing portion is folded over and onto the protecting portion, the second quantity of adhesive substance being made from a transparent material to permit the first and second portions of the surgical instrument and that portion of the patient positioned beneath the passageway to be observed through the viewing portion; a first sheet of protective material to cover the first quantity of adhesive substance, the first sheet including a tab extending beyond the first quantity of adhesive substance by a distance sufficient to allow the tab to be gripped by a finger and thumb encased within a rubber glove; and a second sheet of protective material to cover the second quantity of adhesive substance, the second sheet including a tab extending beyond the second quantity of adhesive substance by a distance sufficient to allow the tab to be gripped by a finger and thumb encased within a rubber glove.

* * * * *